United States Patent [19]
Pennig

[11] Patent Number: 5,709,681
[45] Date of Patent: Jan. 20, 1998

[54] DEVICE FOR OSTEOSYNTHESIS

[76] Inventor: Dietmar Pennig, Hans-Driesch-Strasse 12, Köln, Germany

[21] Appl. No.: 614,742

[22] Filed: Mar. 13, 1996

[30] Foreign Application Priority Data

Sep. 19, 1995 [DE] Germany ............ 295 15 007.6

[51] Int. Cl.$^6$ .................................. A61B 17/60
[52] U.S. Cl. .................. 606/54; 606/57; 606/58; 606/59
[58] Field of Search .................. 606/54, 57, 59, 606/58

[56] References Cited

U.S. PATENT DOCUMENTS

| Re. 34,985 | 6/1995 | Pennig ............... 606/58 |
| 5,160,335 | 11/1992 | Wagenknecht ........ 606/59 |

*Primary Examiner*—Michael Buiz
*Assistant Examiner*—Daphja Shaz
*Attorney, Agent, or Firm*—Hopgood, Calimafde, Kalil & Judlowe

[57] ABSTRACT

A clamping assembly for bone-screw or bone-pin adjustment (a) longitudinally along the guideway of an external fixator, and (b) angularly about a pivot axis at a selected longitudinal location. The clamping assembly comprises a slide block adapted for releasably locked longitudinal positioning along the guideway, an intermediate plate element, and a clamp block, in sandwiched relation, with a single central bolt to secure (i) a selected angular setting of bone-screw engagement grooves coacting between the clamp block and the upper surface of the intermediate plate, and (ii) coacting arcuate tongue-and-groove formations wherein the releasably lockable coaction is between the slide block and the lower surface of the intermediate plate, to secure a given clamped angular orientation of bone-screw orientation with respect to the longitudinal direction of the guideway.

10 Claims, 2 Drawing Sheets

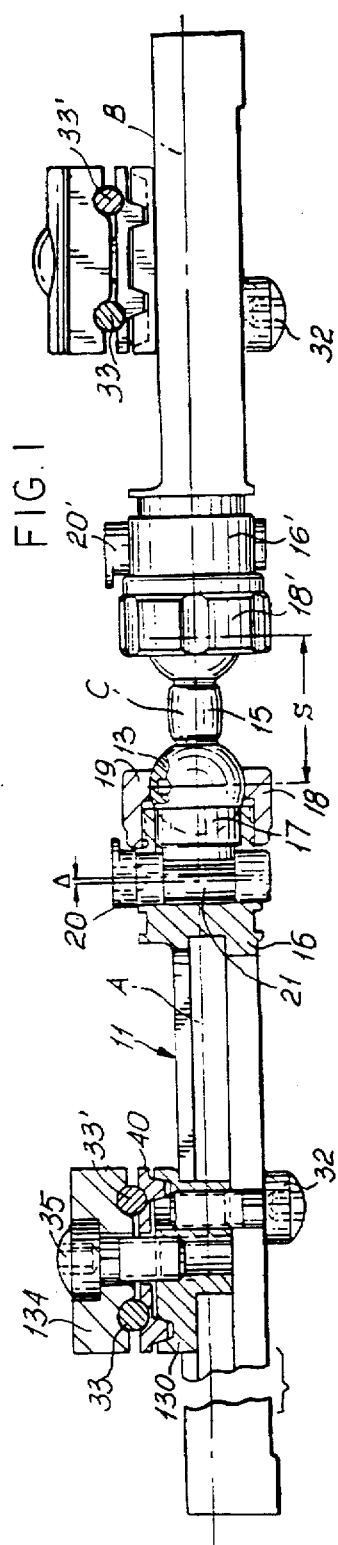
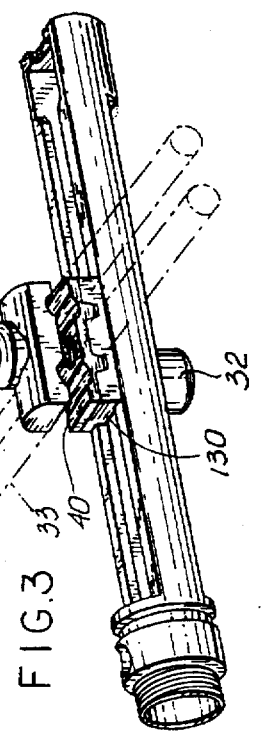
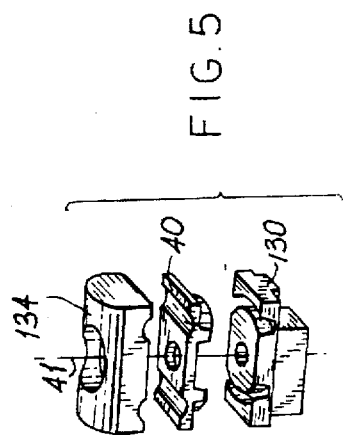
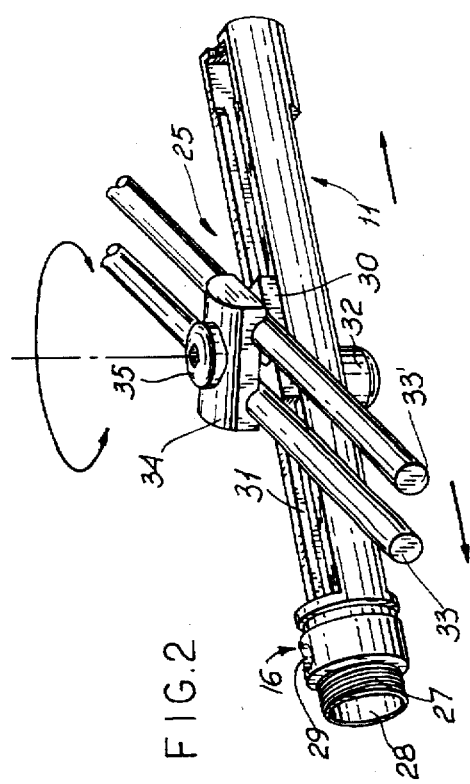
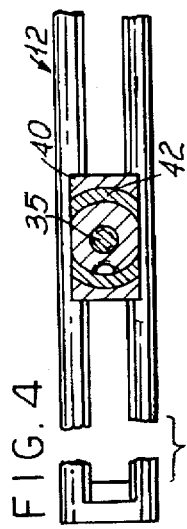

DEVICE FOR OSTEOSYNTHESIS

BACKGROUND OF THE INVENTION

The invention relates to an osteosynthesis aid for the external fixation of segments of a fractured bone. More specifically, the invention pertains to clamping mechanism for bone screws or pins, wherein each of two clamping mechanisms is carried by a different one of two clamp-mounting elements which have spaced and releasably clamped articulatable connection to each other.

U.S. Reissue Pat. No. Re. 34,985 describes an external fixator of the character indicated, wherein each of two elongate supports is a clamp-mounting element, which adjustably carries its own bone-screw clamping mechanism, and these two elongate supports have mutually articulatable interconnection via a so-called double-ball hinge having first releasably clamped ball-joint connection to one of the elongate supports and second releasably clamped ball-joint connection to the other elongate support. The bone-screw clamping mechanism for each elongate support provides a slide block for longitudinally adjustable positioning along the support. The slide block has a flat upper surface, thus providing a flat base surface for clamp action; and a clamp block having two spaced parallel bone-screw engageable grooves in its lower surface is mounted to the flat upper surface (i.e., base surface) of the slide block, via a single clamp bolt, which passes through the clamp block and is engaged to the slide block, to serve as a releasably clamped pivot for the clamp block with respect to the base surface of the slide block. Necessarily, for two bone screws or pins that locate in the bone-screw grooves in confronting relation to the flat upper or base surface of the slide block, there is a wide range for selection of the clamped angular direction of the two bone screws or pins, with respect to the longitudinal direction of the involved elongate support.

In the bone-screw clamps of said reissue patent, the slide block (and thus the flat base surface of the slide block) is rectangular and predominantly elongate in the longitudinal direction of slide adjustability, to assure directional stability of clamped bone-screws or pins. The grooved lower surface of the clamp block is similarly rectangular, and its bone-screw grooves are transverse to the elongate dimension. This relationship necessarily means that the clamped extent of bone-screw or pin mounting will be various for different settings of bone-screw angle with respect to the longitudinal direction of slide-block adjustable displaceability. Thus, for angular settings in which bone-screw or pin mounting is less than the full extent of the grooves of the clamp block, there is a possibility of breakage of the bone screws or pins (and, therefore, loss of external fixation for the involved bone), in the accidental or other delivery of a transverse mechanical shock to the fixated bone; furthermore, the ability to retain a selected angular setting of clamped bone screws or pins will vary, thus inviting slippage of a given angular setting.

BRIEF STATEMENT OF THE INVENTION

It is an object of the invention to provide an improved bone-screw or pin clamp of the character indicated.

A specific object is to achieve the above object in a bone-screw or pin clamp wherein optimally clamped engagement of involved bone screws or clamps is uniform, for all or substantially all possible angular directions of clamped engagement.

It is also a specific object to provide a clamp mechanism of the character indicated having enhanced ability to retain its selected angular setting, without slippage, and over a relatively wide range of adjustability.

Another specific object is to achieve the foregoing objects in the context of an external fixator, especially adapted to fixation of a wrist fracture and therefore of light weight and minimum bulk.

The invention achieves these objects by providing an extra grooved plate member between the clamp block and the base surface of the slide block, wherein the plate member has spaced parallel grooves to match those of the clamp block, so that involved bone screws or pins are positively located (for any and all possible angular adjustments) by and between locating grooves which otherwise confront each other at their symmetrically opposed locations of offset from the pivotal-adjustment axis of the single-clamp bolt.

As a further feature, the invention provides interengaged arcuate groove and rib formations on the plate member and slide block wherein a maximum engaged area of these parts is essentially preserved while, at the same time, the arcuate engagements about the pivot axis enhance the stability of any given resulting selectively adjusted clamping relationship. The result is a clamp system of the indicated character wherein large matching areas of engaged surfaces of the plate member and of the slide block can have maximum area contact for maximum torsional resistance against loss of a given clamped angular setting of the involved bone screws or clamps.

BRIEF DESCRIPTION OF THE DRAWINGS

The preferred and other embodiments of the invention will be described in detail, in conjunction with the accompanying drawings, in which:

FIG. 1 is a fragmentary view in longitudinal section, of an external fixator wherein clamp structure of the invention is adjustably mountable to both ends of the fixator;

FIG. 2 is a perspective view of one end of the fixator of FIG. 1, to show the same equipped with bone-screw clamping mechanism of the prior art;

FIG. 3 is a perspective view similar to FIG. 2, to show bone-screw clamping mechanism of the invention;

FIG. 4 is an enlarged section taken in the plane 4—4 of FIG. 1;

FIG. 5 is an exploded perspective view of the parts of the bone-screw-clamping mechanism of FIG. 1;

DETAILED DESCRIPTION

Figure 6:
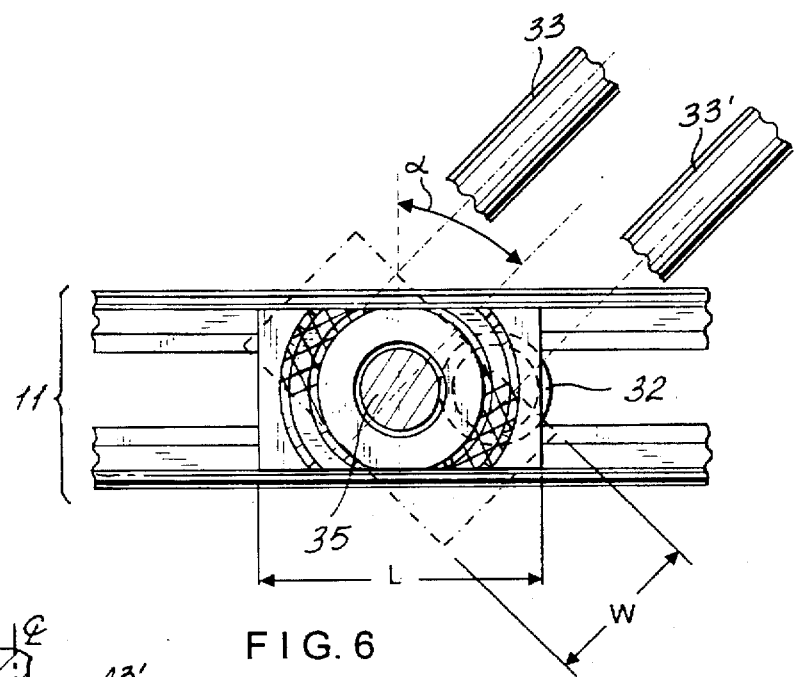
FIG. 6 is a view generally similar to FIG. 4, with schematic further indications to illustrate coaction of parts for an adjusted angular relationship.

In FIG. 1, the presently preferred embodiment of the invention is shown in application to each of the two elongate bone-screw clamp supports 11, 12 at the respective axially spaced ends of an external fixator 10. Adjacent longitudinal ends of the supports 11, 12 have universal double-hinge connection over a short fixed spacing S between centers of double-ball joints which are the means of double-hinge connection. As shown, the fixed connection is between the ball component 13 of one of the ball joints and the ball component 14 of the other ball joint, with a reduced fixed connection 15 therebetween.

The connection 15 has symmetry about a central longitudinal axis C through both ball centers. Socket structures of the confronting head ends of supports 11, 12 have concave spherical formations which respectively engage the ball components 13, 14. In the case of head end 16 of support 11, a cylindrical clamp element 17 is longitudinally guided by a bore in head end 16, concentric with the longitudinal axis A of support 11; clamp element 17 has a concave spherical end face for ball-13 engagement, and an annular clamp-ring element 18, threadedly retained to head end 16, has a radially inward outer-end flange 19 with an inner surface that is also a concave annular portion of a sphere, for axial retention and capture of ball 13 at the head end 16 and centered on the axis A. A transverse pin 20 having an eccentric formation 21 is journalled for externally accessed wrench rotation, to eccentrically drive and thus longitudinally displace clamp element 17 into axially clamped action on ball 13, the same being a squeeze action between oppositely dished portions of a sphere, in the flange 19 of ring 18 and in the end face of element 17. It is noted that the threaded drive of ring 18 to head end 16 is not a clamping engagement but merely an assembly engagement, in that pin 20 rotation is needed for the eccentric displacement Δ to achieve a locking of support 11 to ball 13.

The releasably secured engagement of head end 16' of support 12 to the other ball 14 of the connector is precisely as described for support-11 engagement to ball 14, and corresponding parts are identified by the same reference numbers, having primed notation. In the case of head end 16' of support 12, the ball-joint connection centers ball 14 on the longitudinal axis B of support 12.

FIG. 2 is a perspective view of an adjustable bone-screw clamp 25, of the prior-art construction, for use in a wrist-fixator having an elongate bone-screw clamp support, which may be the support 11 of FIG. 1. The clamp support 11 appears in FIG. 2 with its head end 16 at the left, and exposing its threads 27 for engagement by ring 18, as well as the bores 28, 29 for reception of clamp element 17 and the eccentric locking pin 20, respectively. The bone-screw clamp 25 is seen to comprise a slide block 30 which is formed for selective positioning along a guideway 31 of support 11, and which is clamped by a bolt 32 to retain its longitudinally adjusted position. The upper exposed surface of slide block 30 is flat and rectangular, of width to ride spaced shoulders of the guideway 31 and of length sufficient to receive threads of bolt 32 at a location of longitudinal offset from the longitudinal midpoint of slide block 30. Two spaced bone screws or pins 33, 33' locate in parallel grooves on the underside of a bone-screw clamp block 34 which has overall length and width dimensions to match those of the upper surface of the slide block 30. A bone-screw clamp bolt 35 through the longitudinal center of clamp block 34 will be understood to have threaded engagement to and at the longitudinal center of the slide block, thus rendering the clamp block 34 and its two bone screws or pins 33, 33' rotatably adjustable about bolt 35 until its position is set and clamped by tightening the clamp bolt. In their clamped condition, the bone screws or pins 33, 33' are of course nested in their respective grooves (of clamp block 34), but engagement of the bone screws or pins 33, 33' with the guide block is essentially only by their line of contact with the flat upper surface of the guide block; and the length of each such line contact is a function of the angular setting of bone-screw orientation with respect to the longitudinal direction of support 11. Thus, difficulties are encountered and therefore a problem exists, with respect to the varied nature of clamped bone-screw engagement and support, all as a function of adjusted angle selection.

In accordance with the invention, substantially enhanced clamping effectiveness for bone screws or pins, such as the pins 33, 33', is achieved by addition of an intermediate specially formed plate 40, interposed between a slide block 130 and a clamp block 134, wherein the special formation of plate 40 pertains to the way in which the upper and lower surfaces are characterized for coaction with the clamp-block and slide-block surfaces that they respectively confront.

Specifically, the upper surface of plate 40 is characterized by spaced parallel grooves 133, 133' which are cylindrically arcuate and which are in confronting relation to the spaced parallel grooves on the underside of clamp block 34, to thereby provide double engagements with the respective bone screws 33, 33'. Additionally, the underside of plate 40 is formed with one or more downward convex wedge formations 42, 42' which are arcuate about the vertical axis 41 of adjustable orientation of clamp block 134 and its bone screws (or pins) 33, 33' with respect to the slide block 130; these wedge formations 42, 42' coact with corresponding concave wedge formations 43, 43' in the upper surface of slide block 130, in tongue-and-groove fashion. Thus, the convex wedge formations 42, 42' are both frusto-conical, and in any given diametral plane which includes axis 41, they are preferably of like trapezoidal section. The same may be said about the concave wedge formations 43, 43' of slide block 130, except for the fact that the vertical extent A (see FIG. 7) of the convex formation must be at least equal to, and preferably slightly in excess of the depth B of the concave formation 43, thus providing assurance that clamping of a given desired orientation of the clamp block (and its bone screws or pins) will rely essentially on inner and/or outer cone-to-cone engagements for locking a given angular orientation.

Figure 7:
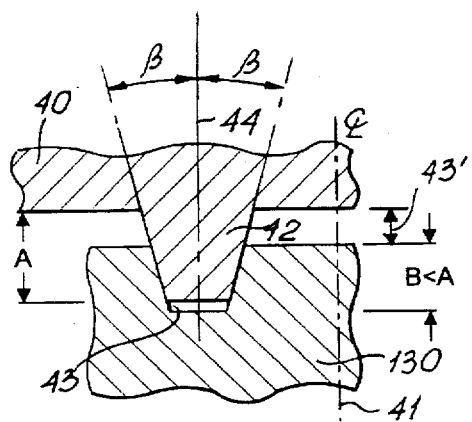
FIG. 7 is a simplified and further enlarged fragmentary view in the longitudinal section plane of FIG. 1, to show a preferred embodiment for selective torsional locking in clamp structure of FIG. 1.

Detail of the above-described, and preferred relationship, for cone-to-cone locked engagements is best seen in the enlarged fragmentary section of FIG. 7, wherein the convex trapezoidal formation 42 is defined by and between equal and opposite slopes β with respect to a geometrically cylindrical surface 44 of symmetry, and wherein the indicated relation of B to A assures axial clearances 43, 43' for the cone-to-cone relation. Suitably, the angle β is in the range 10 to 20 degrees, and is preferably 15 degrees.

Figure 8:
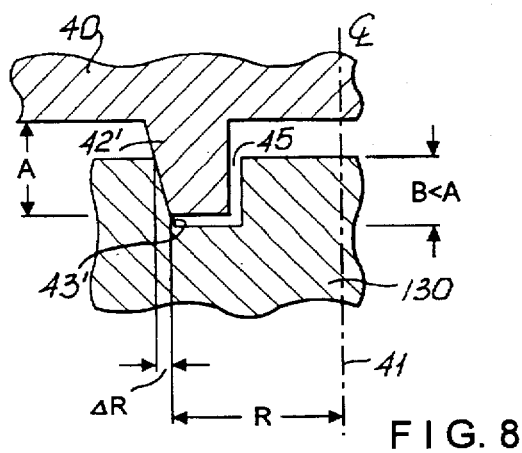
FIG. 8 is a view similar to FIG. 7, for a second embodiment.

In the variation depicted in FIG. 8, there is but a single cone-to-cone wedge engagement, between convex formation 42' and concave formation 43'. This engagement involves coacting outer frusto-conical surfaces, for which engagement commences at a relatively large radius R and extends by ΔR therebeyond. To assure only the cone-to-cone engageability, a radial clearance 45 is shown between parallel confronting inner cylindrical surfaces of the respective convex and concave formations 42', 43'.

Figure 9:
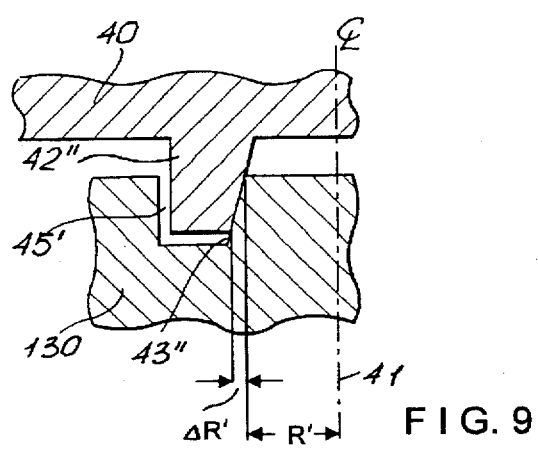
FIG. 9 is another view similar to FIG. 7, for a third embodiment.

In the variation depicted in FIG. 9, there is again only a single cone-to-cone wedge engagement, between convex formation 42" and concave formation 43". This engagement involves coacting inner frusto-conical surfaces, for which engagement commences at a lesser radius R' and extends by ΔR' therebeyond. Again, for assurance of exclusively cone-to-cone engageability, a radial clearance 45' is shown between confronting outer cylindrical surfaces of the respective convex and concave formations 42", 43".

The described invention will be seen to accomplish the objectives stated above. For the most frequently used orientation of clamped bone screws 33, 33' as shown in FIG. 3, i.e., at or close to 90° to the longitudinal axis of slide block 130 (and to the guide axis A of the guide system), the full or substantially the full arcuate extent of both convex/concave engagements is not only available for greatest mechanically locking friction engagement, but these convex/concave engagements develop their friction engagement at totally equal and diametrically opposite areas having symmetry about the adjustment axis 41. And FIG. 6 shows that the equality of diametrically opposite actions also applies for relatively great changes in clamped orientation angle α. Still further, for the mounting system shown wherein the planiform for all three components 130, 40, 134 is substantially the same rectangle (length L, by width W), longitudinal stability derives from the predominant L dimension along the longitudinal guideways of each member 11, 12, while, even for large angular settings α, the essentially longitudinal spacing of the arcuate regions of cone-to-cone engagement is responsible for longitudinal stability of support for the clamped bone screws or pins.

What is claimed is:

1. In a bone-fixator construction comprising two axially elongate end members and a central connecting member, (a) wherein said central connecting member has separate ball-joint connection to one longitiudinal end of each of said end members, the separate connections being on separate spaced centers of ball-joint articulation, (b) wherein each of said end members has an elongate guideway extending beyond the ball-joint-connected end of each said member, and (c) wherein a bone-screw clamp has a base that is axially guided by and positionable in a single plane along each guideway and has provision for selectively clamped rotary orientation of one or more bone screws or bone pins about a feed pivot axis that is normal to said single plane; the improvement in which each bone-screw clamp comprises:

(i) an upper clamp member, an intermediate clamp member end said base, pivotally retained on said pivot axis by a bolt extending centrally through said clamp members and having threaded engagement solely with said base;

(ii) said upper and intermediate clamp members having confronting adjacent surfaces each of which has a pair of bone-screw or bone-pin-engageable groove formations at opposite radial offsets from said pivot axis; and (iii) said intermediate clamp member and said base having confronting adjacent surfaces with tongue-and-groove coacting engagement on a geometric locus which is circular about said pivot axis.

2. The bone-fixator improvement of claim 1, in which said tongue-and-groove engagement comprises a tongue formation having radially spaced inner and outer surfaces concentric with said pivot axis, and a groove formation having radially spaced inner and outer surfaces concentric with said pivot axis, the inner and outer surfaces of said tongue and groove formations being frusto-conical and in mating engagement.

3. The bone-fixator improvement of claim 2, in which, for the bolt-clamped condition of said bone-screw clamp, said tongue formation extends short of axial abutment with the bottom of said groove formation, whereby to assure frictional wedge-lockable coaction between engaged frusto-conical surfaces.

4. The bone-fixator improvement of claim 3, in which said base is of greater longitudinal extent along said guideway and has a lesser transverse dimension, the geometric locus of tongue-and-groove engagement having an outside diameter which is less then said longitudinal extent and greater than said transverse dimension, and said upper and intermediate clamp members having longitudinal and transverse dimensions which substantially register with the respective longitudinal and transverse dimensions of said base when their groove formations are transverse to the longitudinal dimension of said base, whereby, for a range of clamped angular adjustment, greater stability of bone-screw mounting is realizable on diametrically opposed areas of base-to-guideway engagement, for a range of angular settings either side of the transverse orientation when said clamp members and said base are in substantial register.

5. The bone-fixator improvement of claim 4, in which said longitudinal extent is at least substantially 1.5 times said transverse dimension.

6. The bone-fixator improvement of claim 5, in which said longitudinal extent is no greater than substantially twice said transverse dimension.

7. The bone-fixator improvement of claim 1, in which said tongue formation is an axially projecting integral feature of said intermediate clamp member, and in which said groove formation is an integral feature of said base.

8. The bone-fixator improvement of claim 1, in which said tongue-and-groove engagement comprises at least one frusto-conical surface of said tongue in mating engagement with at least one frusto-conical surface of said groove, said frusto-conical surfaces being concentric with said pivot axis.

9. The bone-fixator improvement of claim 1, in which the groove formations of each pair are circumferentially arcuate about said pivot axis.

10. The bone-fixator improvement of claim 1, in which said base is of generally rectangular planiform with a greater longitudinal extent along said guideway and a width dimension which is less than said longitudinal extent, and in which each of said upper and intermediate clamp members has a planiform which substantially conforms to the planiform of said base, the groove formations of each pair being substantially perpendicular to the direction of said longitudinal extent.

\* \* \* \* \*

UNITED STATES PATENT AND TRADEMARK OFFICE
CERTIFICATE OF CORRECTION

PATENT NO. : 5,709,681
DATED : January 20, 1998
INVENTOR(S) : Dietmar PENNIG

It is certified that error appears in the above-indentified patent and that said Letters Patent is hereby corrected as shown below:

Column 5, line 33, before "pivot axis" delete "feed" and insert therefor --fixed--

Column 5, line 37, before "said base" delete "end" and insert therefor --and--

Signed and Sealed this

Fourteenth Day of April, 1998

Attest:

BRUCE LEHMAN

*Attesting Officer*          *Commissioner of Patents and Trademarks*